(12) United States Patent
Zhou et al.

(10) Patent No.: US 8,155,262 B2
(45) Date of Patent: Apr. 10, 2012

(54) METHODS, SYSTEMS, AND COMPUTER PROGRAM PRODUCTS FOR MULTIPLEXING COMPUTED TOMOGRAPHY

(75) Inventors: Otto Z. Zhou, Chapel Hill, NC (US); Jianping Lu, Chapel Hill, NC (US); Jian Zhang, Carrboro, NC (US); Guang Yang, Carrboro, NC (US); Yueh Lee, Durham, NC (US); Qi Qiu, Cary, NC (US); Yuan Cheng, Chapel Hill, NC (US)

(73) Assignees: The University of North Carolina at Chapel Hill, Chapel Hill, NC (US); Xintek, Inc., Research Triangle Park, NC (US)

( * ) Notice: Subject to any disclaimer, the term of this patent is extended or adjusted under 35 U.S.C. 154(b) by 1132 days.

(21) Appl. No.: 11/526,217

(22) Filed: Sep. 22, 2006

(65) Prior Publication Data
US 2010/0239064 A1  Sep. 23, 2010

Related U.S. Application Data

(63) Continuation-in-part of application No. 11/410,997, filed on Apr. 25, 2006, now Pat. No. 7,245,692.

(60) Provisional application No. 60/720,176, filed on Sep. 23, 2005, provisional application No. 60/674,537, filed on Apr. 25, 2005.

(51) Int. Cl.
*A61B 6/03* (2006.01)

(52) U.S. Cl. .................. 378/4; 378/9; 378/19; 378/122; 382/131

(58) Field of Classification Search .................. 378/4, 9, 378/16, 21–26, 62, 98.8, 122
See application file for complete search history.

(56) References Cited

U.S. PATENT DOCUMENTS

| 2,842,706 A | 7/1958 | Dobischek et al. |
| 3,617,285 A | 11/1971 | Staudenmayer |
| 3,733,484 A | 5/1973 | Bayard |

(Continued)

FOREIGN PATENT DOCUMENTS

CN  ZL200680013859.X  1/2011

(Continued)

OTHER PUBLICATIONS

Lalush, Feasibility of Transmission Micro-CT with Two Fan-Beam Sources, Sep. 5, 2004, Proceedings of the 26th Annual international Conference on the IEEE EMBS, pp. 1283-1286.*

(Continued)

*Primary Examiner* — Edward Glick
*Assistant Examiner* — John Corbett
(74) *Attorney, Agent, or Firm* — Jenkins, Wilson, Taylor & Hunt, P.A.

(57) ABSTRACT

Methods, systems, and computer program products for multiplexing computed tomography are disclosed. According to one aspect, the subject matter described herein can include illuminating an object with a plurality of x-ray beams from a plurality of viewing angles, wherein each x-ray beam has a distinct waveform; detecting the x-ray intensities of the plurality of pulsed x-ray beams as a function of time, and extracting individual projection image data from the detected x-ray intensities based on the distinct waveforms of the x-ray beams for combining the projection image data to generate three-dimensional tomographic image data of the object.

13 Claims, 10 Drawing Sheets

U.S. PATENT DOCUMENTS

| | | |
|---|---|---|
| 3,753,020 A | 8/1973 | Zingaro |
| 3,783,288 A | 1/1974 | Barbour et al. |
| 3,921,022 A | 11/1975 | Levine |
| 3,932,756 A | 1/1976 | Cowell et al. |
| 4,012,656 A | 3/1977 | Norman et al. |
| 4,145,614 A | 3/1979 | Kowalski |
| 4,253,221 A | 3/1981 | Cochran, Jr. et al. |
| 4,289,969 A | 9/1981 | Cooperstein et al. |
| 4,382,184 A | 5/1983 | Wernikoff |
| 4,712,226 A | 12/1987 | Horbaschek |
| 4,780,612 A * | 10/1988 | Klatt .......................... 250/336.1 |
| 4,809,308 A | 2/1989 | Adams et al. |
| 4,926,452 A | 5/1990 | Baker et al. |
| 4,958,365 A | 9/1990 | Sohval et al. |
| 5,129,850 A | 7/1992 | Kane et al. |
| 5,138,237 A | 8/1992 | Kane et al. |
| 5,245,648 A | 9/1993 | Kinney et al. |
| 5,305,363 A | 4/1994 | Burke et al. |
| 5,371,778 A | 12/1994 | Yanof et al. |
| 5,377,249 A | 12/1994 | Wiesent et al. |
| 5,390,112 A * | 2/1995 | Tam ................................ 378/17 |
| 5,412,703 A | 5/1995 | Goodenough et al. |
| 5,424,054 A | 6/1995 | Bethune et al. |
| 5,557,105 A | 9/1996 | Honjo et al. |
| 5,578,821 A | 11/1996 | Meisberger et al. |
| 5,594,770 A | 1/1997 | Bowles et al. |
| 5,616,368 A | 4/1997 | Jin et al. |
| 5,623,180 A | 4/1997 | Jin et al. |
| 5,637,950 A | 6/1997 | Jin et al. |
| 5,648,699 A | 7/1997 | Jin et al. |
| 5,692,028 A | 11/1997 | Geus et al. |
| 5,726,524 A | 3/1998 | Debe |
| 5,745,437 A | 4/1998 | Wachter et al. |
| 5,764,683 A | 6/1998 | Swift et al. |
| 5,773,834 A | 6/1998 | Yamamoto et al. |
| 5,773,921 A | 6/1998 | Keesman et al. |
| 5,834,783 A | 11/1998 | Muraki et al. |
| 5,844,963 A | 12/1998 | Koller et al. |
| 5,910,974 A | 6/1999 | Kuhn et al. |
| 5,973,444 A | 10/1999 | Xu et al. |
| RE36,415 E | 11/1999 | McKenna |
| 5,976,444 A | 11/1999 | Pearson et al. |
| 6,019,656 A | 2/2000 | Park et al. |
| 6,028,911 A | 2/2000 | Kawahara |
| 6,057,637 A | 5/2000 | Zettl et al. |
| 6,087,765 A | 7/2000 | Coll et al. |
| 6,097,138 A | 8/2000 | Nakamoto |
| 6,097,788 A | 8/2000 | Berenstein et al. |
| 6,125,167 A | 9/2000 | Morgan |
| 6,178,226 B1 | 1/2001 | Hell et al. |
| 6,192,104 B1 | 2/2001 | Adams et al. |
| 6,250,984 B1 | 6/2001 | Jin et al. |
| 6,259,765 B1 | 7/2001 | Baptist |
| 6,271,923 B1 | 8/2001 | Hill |
| 6,277,318 B1 | 8/2001 | Bower et al. |
| 6,280,697 B1 | 8/2001 | Zhou et al. |
| 6,297,592 B1 | 10/2001 | Goren et al. |
| 6,333,968 B1 | 12/2001 | Whitlock et al. |
| 6,334,939 B1 | 1/2002 | Zhou et al. |
| 6,350,628 B1 | 2/2002 | Cheng et al. |
| 6,376,973 B1 | 4/2002 | Blanchet-Fincher et al. |
| 6,385,292 B1 | 5/2002 | Dunham et al. |
| 6,440,761 B1 | 8/2002 | Choi |
| 6,445,122 B1 | 9/2002 | Chuang et al. |
| 6,456,691 B2 | 9/2002 | Takahashi et al. |
| 6,459,767 B1 | 10/2002 | Boyer et al. |
| 6,470,068 B2 | 10/2002 | Cheng |
| 6,498,349 B1 | 12/2002 | Thomas et al. |
| 6,510,195 B1 | 1/2003 | Chappo et al. |
| 6,529,575 B1 * | 3/2003 | Hsieh ................................ 378/4 |
| 6,545,396 B1 | 4/2003 | Ohki et al. |
| 6,553,096 B1 | 4/2003 | Zhou et al. |
| 6,560,309 B1 | 5/2003 | Becker et al. |
| RE38,223 E | 8/2003 | Keesmann et al. |
| 6,621,887 B2 | 9/2003 | Albagli et al. |
| 6,630,772 B1 | 10/2003 | Bower et al. |
| 6,650,730 B2 | 11/2003 | Bogatu et al. |
| 6,672,926 B2 | 1/2004 | Liu et al. |
| 6,674,837 B1 | 1/2004 | Taskar et al. |
| 6,754,300 B2 * | 6/2004 | Hsieh et al. ....................... 378/16 |
| 6,760,407 B2 | 7/2004 | Price et al. |
| RE38,561 E | 8/2004 | Keesmann et al. |
| 6,787,122 B2 | 9/2004 | Zhou |
| 6,850,595 B2 | 2/2005 | Zhou et al. |
| 6,852,973 B2 | 2/2005 | Suzuki et al. |
| 6,876,724 B2 | 4/2005 | Zhou et al. |
| 6,950,493 B2 | 9/2005 | Besson |
| 6,965,199 B2 | 11/2005 | Stoner et al. |
| 6,980,627 B2 | 12/2005 | Qiu et al. |
| 7,027,558 B2 | 4/2006 | Ghelmansarai et al. |
| 7,046,757 B1 | 5/2006 | Bani-Hashemi et al. |
| 7,082,182 B2 | 7/2006 | Zhou et al. |
| 7,085,351 B2 | 8/2006 | Lu et al. |
| 7,147,894 B2 | 12/2006 | Zhou et al. |
| 7,220,971 B1 | 5/2007 | Chang et al. |
| 7,227,924 B2 | 6/2007 | Zhou et al. |
| 7,245,692 B2 | 7/2007 | Lu et al. |
| 7,359,484 B2 | 4/2008 | Qiu et al. |
| 7,420,174 B2 * | 9/2008 | Kurita et al. ................. 250/358.1 |
| 7,741,624 B1 | 6/2010 | Sahadevan |
| 7,751,528 B2 | 7/2010 | Zhou et al. |
| 7,835,492 B1 | 11/2010 | Sahadevan |
| 7,902,530 B1 | 3/2011 | Sahadevan |
| 2001/0019601 A1 | 9/2001 | Tkahashi et al. |
| 2002/0085674 A1 | 7/2002 | Price et al. |
| 2002/0094064 A1 * | 7/2002 | Zhou et al. ....................... 378/122 |
| 2002/0110996 A1 | 8/2002 | Yaniv et al. |
| 2002/0140336 A1 | 10/2002 | Stoner et al. |
| 2002/0159565 A1 | 10/2002 | Muller et al. |
| 2002/0171357 A1 | 11/2002 | Sun et al. |
| 2002/0191751 A1 | 12/2002 | Bogatu et al. |
| 2002/0193040 A1 | 12/2002 | Zhou |
| 2003/0002627 A1 | 1/2003 | Espinosa et al. |
| 2003/0002628 A1 | 1/2003 | Wilson et al. |
| 2003/0048868 A1 | 3/2003 | Bailey et al. |
| 2003/0102222 A1 | 6/2003 | Zhou et al. |
| 2003/0103666 A1 | 6/2003 | Edic et al. |
| 2003/0142790 A1 | 7/2003 | Zhou et al. |
| 2003/0198318 A1 | 10/2003 | Price et al. |
| 2004/0017888 A1 | 1/2004 | Seppi et al. |
| 2004/0036402 A1 | 2/2004 | Keesmann et al. |
| 2004/0065465 A1 | 4/2004 | Chappo et al. |
| 2004/0108298 A1 | 6/2004 | Gao |
| 2004/0114721 A1 | 6/2004 | Qiu et al. |
| 2004/0213378 A1 | 10/2004 | Zhou et al. |
| 2004/0240616 A1 | 12/2004 | Qiu et al. |
| 2004/0256975 A1 | 12/2004 | Gao et al. |
| 2005/0028554 A1 | 2/2005 | Wanner et al. |
| 2005/0084073 A1 * | 4/2005 | Seppi et al. .................... 378/156 |
| 2005/0117701 A1 | 6/2005 | Nelson et al. |
| 2005/0133372 A1 | 6/2005 | Zhou et al. |
| 2005/0175151 A1 | 8/2005 | Dunham et al. |
| 2005/0226361 A1 | 10/2005 | Zhou et al. |
| 2005/0226371 A1 | 10/2005 | Kantzer et al. |
| 2005/0269559 A1 | 12/2005 | Zhou et al. |
| 2006/0018432 A1 * | 1/2006 | Zhou et al. ....................... 378/122 |
| 2006/0291711 A1 | 12/2006 | Jabri et al. |
| 2007/0009081 A1 | 1/2007 | Zhou et al. |
| 2008/0031400 A1 | 2/2008 | Beaulieu et al. |
| 2008/0069420 A1 | 3/2008 | Zhang et al. |
| 2010/0329413 A1 | 12/2010 | Zhou et al. |

FOREIGN PATENT DOCUMENTS

| | | |
|---|---|---|
| CN | ZL200810215733 | 10/2011 |
| EP | 0 268 488 | 5/1988 |
| EP | 1 050 272 A1 | 11/2000 |
| EP | 0 648 468 | 4/2005 |
| GB | 679617 | 9/1952 |
| JP | 09180894 A | 7/1997 |
| JP | 11-111158 | 4/1999 |
| JP | 11-260244 | 9/1999 |
| JP | 08264139 A | 10/1999 |
| JP | 2000208028 | 7/2000 |
| JP | 2001190550 A | 7/2001 |
| TW | 00319886 | 11/1997 |
| WO | WO 00/51936 A3 | 9/2000 |
| WO | WO 02/03413 | 1/2002 |

| WO | WO 02/31857 | 4/2002 |
| --- | --- | --- |
| WO | WO 03/012816 A2 | 2/2003 |
| WO | WO 2004/061477 | 7/2004 |
| WO | WO 2004096050 A1 * | 11/2004 |
| WO | WO 2004097889 A2 * | 11/2004 |
| WO | WO 2005/079246 | 1/2005 |

OTHER PUBLICATIONS

Lee et al., Novel Micro-CT based on a Carbon Nanotube Field Emission X-ray Source, Nov. 30, 2003, 2003 Radiological Society of North American meeting, Abstract code A21-182.*
Jerri, The Shannon Sampling Theorem—Its Various extensions and Applications: A Tutorial review, 1977, IEEE, v65, No. 11, pp. 1565-1596.*
Cheng et al., Electron field emission from carbon nanotubes, 2003, C.R. Physique, pp. 1021-1033.*
Weisstein, CRC Concise Encyclopedia of Mathematics, second edition, 2003, pp. 1, 54, 1092-1097, 1936, 2046 and 2615.*
Shannon, Communication in the presence of Noise, 1998, IEEE, vol. 86, No. 2, pp. 447-108.*
Nyquist, Certain Topics in Telegraphic Transmission Theory, 2002, IEEE, vol. 2, No. 2, pp. 208-305.*
Kruger et al., Tomosynthesis Applied to Digital Subtraction Angiography, 1984, Radiology, V152, pp. 805-808.*
Feldkamp et al., "Practical cone-beam algorithm", 1984, Journal of the Optical Society of America, vol. 1, No. 6, pp. 612-619.*
Cheng et al., "Dynamic radiography using a carbon-nanotube-based field-emission x-ray source,", Oct. 2004, Review of Scientific Instruments, vol. 75, No. 10: pp. 3264-3267.*
Lee et al., "Pulsed X-ray Imaging of Small Animals using a Carbon Nanotube based X-ray Source", presented at Academy of Molecular Imaging Annual Meeting, Orlando, FL, Mar. 2004, Molecular Imaging and Biology, vol. 6, No. 2, Abstract No. 41, p. 80.*
International Search Report for PCT/US06/37046 dated May 21, 2007.
First Office Action from Chinese Patent Office for Chinese Patent Application Serial No. 200680013859.X dated Sep. 25, 2009.
Bentley, M.D. et al., "The Use of Microcomputed Tomography to Study Microvasculature in Small Rodents", Am. J Physiol Regulatoty Integrative Comp Physiol, 282, pp. R1267-1279, 2002.
Bonard et al., "Field emission from single-wall carbon nanotube films", Appl. Phys. Left., vol. 73, No. 7, pp. 918-920 (Aug. 17, 1998).
Bower et al., "Synthesis and structure of pristine and alkali-metal-intercalated single-walled carbon nanotubes", Appl. Phys., A 67, pp. 47-52 (1998).
Bower, C. et al., "Fabrication and Field Emission Properties of Carbon Nanotube Cathodes", Mat. Res. Soc. Symp. Proc., vol. 593, pp. 215-220, 2000.
Brock et al., "Hadamard Transform Time-of-Flight Mass Spectrometry," Analytical Chemistry, vol. 70, No. 18, Sep. 15, 1998.
Brodie et al., "Vacuum Microelectronics", Advance in Electronics and Electron Physics, edited by P.W. Hawkes, vol. 83, pp. 1-106 (1992).
Bushong, S.C., "Radiologic Science for Technologist," Physics, Biology, and Protection, 6th Edition, Mosby, Inc., 1997. pp. 107-125.
Cassell et al., "Large Scale CVD Synthesis of Single-Walled Carbon Nanotubes", J. Phys. Chem., B 103, pp. 6484-6492 (Jul. 20, 1999).
Charbonnier et al., "Resolution of Field-Emmision X-Ray Sources," Radiology, vol. 117: pp. 165-172 (Oct. 1975).
Cheng et al., "Dynamic radiography using a carbon-nanotube-based field source," Review of Scientific Instruments, vol. 75, No. 10: pp. 3264-3267 (Oct. 2004).
de Heer et al., "A Carbon Nanotube Field-Emission Electron Source", Science, vol. 270, pp. 1179-1180 (Nov. 17, 1995).
Dobbins III et al., "Digital x-ray tomosynthesis: current state of the art and clinical potential," Phys. Med. Biol. 48 (2003) R65-R106.
Feldkamp L.A. et al., "Practical Cone-Beam Algorithm", J. Opt. Soc. Am., 1(a):612-619, 1984.

Gao et al., "Fabrication and Electron Field Emmision Properties of Carbon Nanotube Films by Electrophoretic Deposition," Advanced Materials, vol. 13, No. 23 (2001).pp. 1770-1773.
Geis et al., "Diamond emitters fabrication and theory", J. Vac. Sci. Technol. B, vol. 14, No. 3, pp. 2060-2067, May/Jun. 1996.
Hallenbeck, "Clinical Evaluation of the 350-kV Chest Radiography System," Radiology, vol. 117: pp. 1-4 (1974).
Hu, J. et al., "Chemistry and Physics in One Dimension: Synthesis and Properties of Nanowires and Nanotubes", Accounts of Chemical Research, vol. 32, pp. 435-445, 1999.
Journet et al., "Large-scale production of single-walled carbon nanotubes by the electric-arc technique", Nature, vol. 388, pp. 756-760 (Aug. 21, 1997).
Kumar et al., "Diamond-based field emission flat panel displays", Solid State Technology, vol. 38, pp. 71-74 (May 1995).
Moore et al., "Three-Dimensional X-Ray Laminography as a Tool for Detection and Characterization of BGA Package Defects", IEEE Transactions on Components and Packaging Technologies. vol. 25, No. 2, Jun. 2002, pp. 224-229.
Okano et al., "Electron emission from nitrogen-doped pyramidal-shape diamond and its battery operation", Appl. Phys. Lett., vol. 70, No. 16, pp. 2201-2203 (Apr. 21, 1997).
Okano et al., "Fabrication of a diamond field emitter array", Appl. Phys. Lett., vol. 64, No. 20, pp. 2742-2744 (May 16, 1994).
Okazaki et al., "A New Emission Spectrum of $Au_2$ in the Gas Evaporation Technique: 761-809 nm", Jpn. J. Appl. Phys., vol. 37, Pt. 1, No. 1, pp. 349-350 (Jan. 1998).
Resat et al., "Microbeam developments and applications: A low linear energy transfer perspective," Cancer and Metastasis Reviews 23: p. 323-331 (2004).
Ribbing et al., "Diamond membrane based sructures for miniature X-ray sources," Diamond and Related Materials, vol. 11: pp. 1-7 (2002).
Rinzler et al., "Unraveling Nanotubes: Field Emission from an Atomic Wire", Science, vol. 269, pp. 1550-1553 (Sep. 15, 1995).
Saito, Y. et al., "Field Emission Patterns from Single-Walled Carbon Nanotubes", Jpn. J. Appl. Phys., vol. 36, pp. L1340-L1342, Part 2, No. 10A, Oct. 1, 1997.
Saito, Y. et al., "Cathode Ray Tube Lighting Elements with Carbon Nanotube Field Emitters", Jpn. J. Appl. Phys., vol. 37, pp. L346-L348, Part 2, No. 3B, Mar. 15, 1998.
Sloane, "Multiplexing Methods in Spectroscopy," Mathematics Magazine, vol. 52, No. 2 (Mar. 1979), 71-80.
Sugie et al., "Carbon nanotubes as electron source in an x-ray tube," Applied Physics Letters, vol. 78, No. 17: pp. 2578-2580 (2001).
Tang, X. P. et al., "Electronic Structures of Single-Walled Carbon Nanotubes Determined by NMR", Science, vol. 288, pp. 492-494 (Apr. 21, 2000).
Thess, A. et al., "Crystalline Ropes of Metallic Carbon Nanotubes", Science, vol. 273, pp. 483-487 (Jul. 26, 1996).
Traedo, "A Thousand Points of Light: The Hadamard Transform in Chemical Analysis and Instrumentation," Analytical Chemistry. vol. 61, No. 11, Jun. 1, 1989.
Vogel et al., "A New Method of Multiplanar Emission Tomography using a Seven Pinhole Collimator and an Anger Scintillation Camera," Jour. Nuclear Medicine, vol. 19, No. 6, pp. 648-654, 1978.
Wang et al., "Field Emission From Nanotube Bundle Emitters at Low Fields", App. Phys. Lett., 70(24), pp. 3308-3310, Jun. 16, 1997.
Wang et al., "A nanotube-based field-emission flat panel display", Appl. Phys. Lett., vol. 72, No. 2, pp. 2912-2913 (Jun. 1, 1998).
Weinstein et al., "Data Transmission by Frequency-Division Multiplexing Using the Discrete Fourier Transform," IEEE Trans. on Commun. Tech., vol. Com-19, No. 5, pp. 628-634, Oct. 1971.
Yagishita et al., "Effects of Cleavage on Local Cross-Sectional Stress Distribution in Trench Isolation Structure", Jpn. J. Appl. Phys., vol. 36, pp. 1335-1340 (Mar. 1997).
Yue et al., "Generation of continuous and pulsed diagnostic imaging x-ray radiation using a carbon nontube based field emission cathode," Applied Physics Letters, vol. 81, No. 2: pp. 355-357 (F) Jul. 8, 2002.
Zhang et al., "Multiplexing radiography using a carbon nanotube based x-ray source," Applied Physics Letters, vol. 89, 2006, pp. 064106-1 to 064106-3.

Zhang et al., "Stationary scanning x-ray source based on carbon nanotube field emitters," Applied Physics Letters, vol. 86, 2005, pp. 184104-1 to 184104-3.

Zhou et al., "Materials Science of Carbon Nanotubes: Fabrication, Integration, and Properties of Macroscopic Structures of Carbon Nanotubes", *Acc. Chem. Res.*, vol. 35, pp. 1045-1053, 2002.

Zhu et al., "Low-Field Electron Emission from Updoped Nanostructured Diamond", *Science*, vol. 282, 1471-1473 (Nov. 20, 1998).

Zhu, W. et al., "Large Current Density from Carbon Nanotube Filed Emitters", *Appl. Phys. Lett.*, American Institute of Physics, vol. 75, No. 6, Aug. 9, 1999, pp. 873-875.

Non-final Office Action for U.S. Appl. No. 09/679,303 dated Jan. 16, 2002.

Final Office Action for U.S. Appl. No. 09/679,303 dated May 6, 2002.

Non-final Office Action for U.S. Appl. No. 09/679,303 dated Aug. 20, 2002.

Notice of Allowance for U.S. Appl. No. 09/679,303 dated Nov. 1, 2002.

Office Communication for U.S. Appl. No. 09/679,303 dated Feb. 6, 2003.

International Search Report for Application No. PCT/US03/00537 dated Apr. 10, 2003.

Non-final Office Action for U.S. Appl. No. 10/309,126 dated May 22, 2003.

Non-final Office Action for U.S. Appl. No. 10/051,183 dated Sep. 10, 2003.

Non-final Office Action for U.S. Appl. No. 10/309,126 dated Nov. 5, 2003.

Non-final Office Action for U.S. Appl. No. 10/309,126 dated Apr. 20, 2004.

Non-final Office Action for U.S. Appl. No. 10/051,183 dated Apr. 21, 2004.

Notice of Allowance for U.S. Appl. No. 10/309,126 dated Aug. 26, 2004.

Notice of Allowance for U.S. Appl. No. 10/051,183 dated Aug. 31, 2004.

Corrected Notice of Allowance for U.S. Appl. No. 10/309,126 dated Sep. 14, 2004.

Non-final Office Action for U.S. Appl. No. 10/358,160 dated Sep. 21, 2004.

Office Communication for U.S. Appl. No. 10/051,183 dated Jan. 14, 2005.

International Search Report and Written Opinion for PCT/US04/12660 dated Apr. 7, 2005.

Non-final Office Action U.S. Appl. No. 10/358,160 dated Jun. 7, 2005.

Office Action-Restriction requirement U.S. Appl. No. 10/358,160 dated Oct. 26, 2005.

Notice of Allowance U.S. Appl. No. 10/358,160 dated Feb. 8, 2006.

International Search Report and Written Opinion for Application No. PCT/U505/03991 dated Jun. 22, 2006 / Aug. 14, 2006.

Non-Final Office Action for U.S. Appl. No. 11/320,515 dated Aug. 17, 2006.

Office Action-Restriction requirement for U.S. Appl. No. 11/051,332 dated Sep. 7, 2006.

International Search Report for corresponding International Application No. PCT/US05/47066 dated Oct. 6, 2006.

Notice of Allowance dated for U.S. Appl. No. 11/051,332 dated Dec. 28, 2006.

International Preliminary Report on Patentability for PCT/US04/12660 dated May 9, 2007.

Korean Intellectual Property Office (KIPO) Office Action for Korean Patent Application No. 10-2004-7011373 dated Jun. 11, 2007.

European Patent Office Examination Report dated Jun. 28, 2007 for European Patent Application No. 03702044.3.

Korean Intellectual Property Office (KIPO) Office Action for Korean Patent Application No. 10-2003-700004987 dated Jul. 19, 2007.

Second Chinese Office Action for Patent Application No. 03806739.0 dated Oct. 19, 2007.

Non-final Office Action for U.S. Appl. No. 11/415,953 dated Dec. 11, 2007.

Korean Office Action for Korean Patent Application No. 10-2004-7011373 dated Dec. 18, 2007.

Taiwanese Office Action for Taiwan Patent No. 093102622 dated Dec. 21, 2007.

Examination Report from European Patent Office dated Mar. 3, 2008 for European Patent Application No. 03702044.3.

Third Chinese Office Action dated Mar. 14, 2008 for Chinese Patent Application No. 01820211.X (PCT/US01/30027).

Non-final Office Action for U.S. Appl. No. 10/970,384 dated Apr. 8, 2008.

Office Action-Restriction requirement for U.S. Appl. No. 11/415,953 dated May 22, 2008.

Office Action from Canadian Patent Office dated May 27, 2008 for Canadian Application No. 2,424,826.

Japanese Patent Office Action for JP No. 2003-562962 for corresponding PCT No. US03/00537 dated Jun. 20, 2008.

Office Action from Japanese Patent Office for Japanese Patent Application No. 2003-580561 for corresponding PCT No. US03/06345 dated Sep. 3, 2008.

International Search Report and Written Opinion for PCT Application No. PCT/US08/70477 dated Oct. 1, 2008.

First Office Action from Japanese Patent Office for Japanese Patent Application No. 2002-535152, based on PCT/US01/30027 dated Oct. 17, 2008.

First Office Action from Japanese Patent Office dated Jan. 6, 2009 for JP Application No. 2006-513282.

Notice of Publication for Chinese Patent Application No. 200810215733.1 (Publication No. 101352353) dated Jan. 28, 2009.

Confirmation of issuance of Chinese Patent No. ZL01820211.X corresponding to PCT/US01/30027 dated Feb. 4, 2009.

Confirmation that Chinese Application 093102622 issued on Mar. 1, 2009 as Patent No. TW I307110.

First Office Action from Chinese Patent Office dated Mar. 6, 2009 for Chinese Patent Application No. 200480017120.7.

Japanese Final Office Action for Japanese Patent Application No. 2003-562962 based on PCT/US03/00537 dated Mar. 30, 2009.

First Office Action from Chinese Patent Office for Chinese Patent Application No. 200710003710.X dated Apr. 24, 2009.

Office Action-Final for U.S. Appl. No. 11/441,281 dated Jun. 4, 2009.

Supplementary European Search Report for European Patent Application No. 01981327.8 dated Jun. 22, 2009.

Non-Final Office Action for 12/176,056 dated Sep. 2, 2009.

Supplementary European Search report dated Oct. 7, 2009 for EPO Application No. 04 77 5902 (PCT/US2004012660).

Second Office Action from Japanese Patent Office dated Dec. 7, 2009 for Japanese Patent Application No. 2002-535152.

Decision on Rejection issued from the Chinese Patent Office dated Dec. 11, 2009 for Chinese Application No. 200710003710.X.

Non-final Office Action for U.S. Appl. No. 11/441,281 dated Jan. 11, 2010.

Second Office Action corresponding to Chinese Patent Application No. 200680013859 dated Apr. 30, 2010.

First Office Action corresponding to Chinese Patent Application No. 200680043786.9 dated Jul. 6, 2010.

Final Office Action for U.S. Appl. No. 11/441,281 dated Sep. 30, 2010.

Non-Final Office Action for U.S. Appl. No. 11/804,897 dated Nov. 8, 2010.

Second Office Action for CN Appl. No. 2004-80017120.7 dated Nov. 17, 2010.

Third Office Action for CN Appl. No. 2008-10215733.1 dated Dec. 14, 2010.

Non-Final Office Action for U.S. Appl. No. 11/441,281 dated Mar. 15, 2011.

U.S. Appl. No. 12/655,825, filed Jan. 7, 2010 entitled "System and Method for All Field Simultaneous Radiation Therapy and Concealed Object Screening. . ."

Third-Party Submission against U.S. Appl. No. 12/688,425 dated Feb. 28, 2011.

Second Office Action for CN Appl. No. 2006-80043786.9 dated Mar. 2, 2011.

First Office Action for CN Appl. No. 200880107680.X dated Apr. 7, 2011.
Notification to Grant for Chinese Patent Application No. 200810215733.1 dated Jun. 2, 2011.
Notification to Grant for Chinese Patent Application No. 200480017120.7 dated Jul. 12, 2011.
Final Office Action for U.S. Appl. No. 11/804,897 dated Jul. 14, 2011.
Japanese Office Action for JP Appl. No. 2008-532428 dated Sep. 20, 2011.
Non-Final Office Action for U.S. Appl. No. 11/441,281 dated Oct. 19, 2011.
European Search Report for EP 06815214 dated Oct. 25, 2011.

* cited by examiner

METHODS, SYSTEMS, AND COMPUTER PROGRAM PRODUCTS FOR MULTIPLEXING COMPUTED TOMOGRAPHY

RELATED APPLICATIONS

This application claims the benefit of U.S. Provisional Patent Application Ser. No. 60/720,176, filed Sep. 23, 2005. This application is also a continuation-in-part of U.S. patent application Ser. No. 11/410,997, filed Apr. 25, 2006 now U.S. Pat. No. 7,245,692, which claims priority to U.S. Provisional Patent Application Ser. No. 60/674,537, filed Apr. 25, 2005. The disclosures of each of the above applications are incorporated by reference herein in their entireties.

GRANT STATEMENT

This work was supported at least in part by grants from the National Institute of Health and the National Institute of Biomedical Imaging and Bioengineering (NIH-NIBIB) (Grant No. 1-R21-EB004204-01), and the National Institute of Cancer (NCI) (Grant No. U54CA119343). The U.S. government may have certain rights in the present disclosure.

TECHNICAL FIELD

The subject matter described herein relates to imaging. More specifically, the subject matter describes methods, systems and computer program products for multiplexing computed tomography.

BACKGROUND

X-ray radiation is widely used to probe the internal structure of materials in applications such as medical diagnosis, security screening, and industrial inspection. In simple imaging methods, x-ray photons are transmitted through an object. The transmitted x-ray photons collected by a recording device over a period of time to form a static projection image with overlapping structural features. More advanced imaging methods, such as computed tomography (CT), use multiple projection images from different viewing angles for image reconstruction or multiple frame images for contrast enhancement purposes.

Typical CT scanners achieve multiple viewing angles by high-speed rotation of an x-ray tube around an object. This requires a large and complicated gantry, which limits current medical CT scanners to about one second per scan. This sequential recording of x-ray images is inefficient when a large number of images of the same object are required. For example, CT scanners with a single-pixel x-ray tube take about 0.5 seconds for the x-ray tube to make one 360 degree rotation. In the process of this one rotation, about 1,000-2,000 projection images are taken. Each exposure is roughly 250-500 µs. For applications such as medical imaging, the long exposure times of current CT systems make them undesirable or ineffective.

Techniques for increasing data collection speed for single-pixel x-ray tube systems include increasing the rotation speed of the x-ray tube or increasing the x-ray flux. However, these techniques are limited by physical constraints regarding the maximal rotation speed of the x-ray tube and overheating of the anode surface.

Accordingly, in light of the above described difficulties and needs associated with x-ray imaging, there exists a need for improved methods, systems, and computer program products for multiplexing computed tomography.

SUMMARY

The subject matter described herein comprises methods, systems and computer program products for performing multiplexing computed tomography. One aspect can include an x-ray generating device configured to simultaneously generate a plurality of x-ray beams having distinct waveforms and configured to transmit the x-ray beams toward an object from a plurality of different viewing angles. An x-ray detector can be provided operable to detect x-ray intensities of the plurality of x-ray beams as a function of time and an image processing module operable to extract individual projection image data from the detected x-ray intensities based on the distinct waveforms of the x-ray beams for combining the projection image data to generate three-dimensional tomographic image data of the object according to an aspect of the subject matter described herein.

The subject matter described herein can be implemented using a computer program product comprising computer executable instructions embodied in a computer readable medium. Exemplary computer readable media suitable for implementing the subject matter described herein can include chip memory devices, disc memory devices, application specific integrated circuits, and programmable logic devices. In addition, a computer program product that implements a subject matter described herein can reside on a single device or computing platform or can be distributed across multiple devices or computing platforms.

BRIEF DESCRIPTION OF THE DRAWINGS

The subject matter described herein will now be explained with reference to the accompanying drawings of which.

DETAILED DESCRIPTION

The subject matter disclosed herein describes systems, methods and computer program products for multiplexing CT. The subject matter described herein can have particular application for use in radiographic imaging, including CT, tomosynthesis, fluoroscopy, and angiography. A multiplexing CT system according to the subject matter described herein can include an x-ray generating device configured to simultaneously generate a plurality of x-ray beams having distinct waveforms and configured to transmit the x-ray beams toward an object from a plurality of different viewing angles. Further, a multiplexing computed tomography system according to the subject matter described herein can include an x-ray detector to detect x-ray intensities of the plurality of x-ray beams as a function of time. Further, a multiplexing CT system according to the subject matter described herein can include an image processing module to extract individual projection image data from the detected x-ray intensities based on the distinct waveforms of the x-ray beams for combining the projection image data to generate three-dimensional tomographic image data of the object.

In one aspect, a multiplexing computed tomography system according to the subject matter described herein can simultaneously generate pixellated x-ray beams with programmable waveforms and direct the x-ray beams to an object to be imaged. The x-ray beams can be generated by a multi-beam field emission x-ray (MBFEX) source. The x-ray beams can be detected by a digital x-ray detector. An image processing module can be operable to extract individual projection data from the detected x-rays based on the waveforms of the x-rays for combining the projection image data to generate three-dimensional tomographic image data of the object. The parallel imaging process may be advantageous, for example, because it can reduce the total data collection time for CT imaging and the x-ray intensity required from the x-ray source. In one example, the x-ray beams can each be generated by single-pixel x-ray sources using carbon nanotube (CNT) based field emission cathodes, which have the capability for generating x-rays with programmable waveforms where the intensity, pulse width and repetition rate can be readily varied.

An exemplary CNT-based field emission cathode x-ray generating device is described in U.S. Pat. No. 6,876,724 (entitled "Large-Area Individually Addressable Multi-Beam X-Ray System and Method of Forming Same"), the disclosure of which is incorporated herein by reference in its entirety. This patent discloses an x-ray-generating structure having a plurality of stationary and individually electrically addressable field emissive electron sources with a substrate composed of a field emissive material, such as carbon nanotubes. The x-ray generating devices disclosed in this patent are an example of x-ray generating devices that can be used in accordance with the subject matter described herein.

Figure 1:
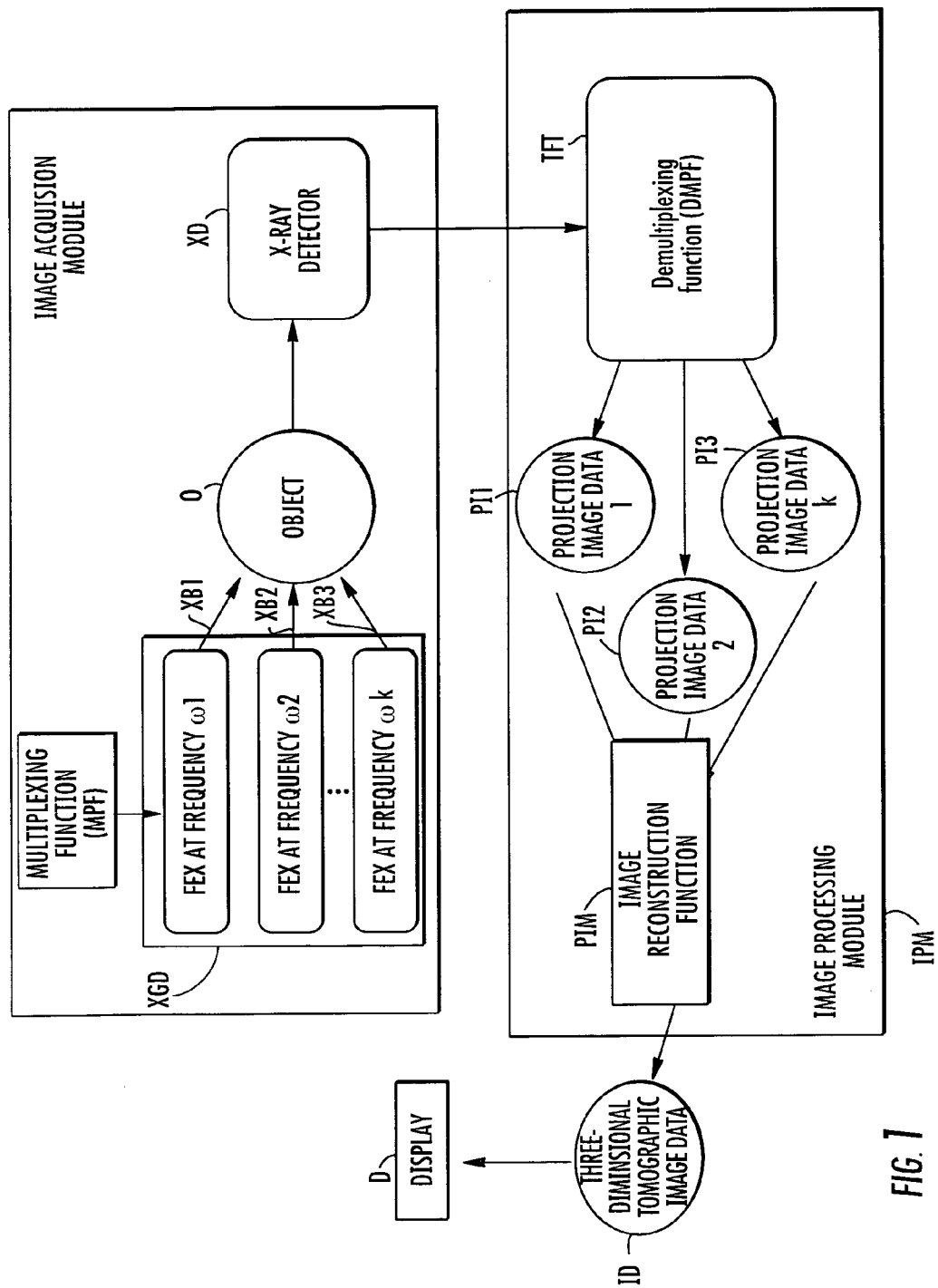
FIG. 1 is a block diagram of one example of a multiplexing computed tomography system according to the subject matter described herein.

FIG. 1 is a block diagram of an exemplary multiplexing computed tomography system generally designated 100 according to one aspect of the subject matter described herein. System 100 can collect three-dimensional tomographic image data ID of an object O. To collect image data ID, a multiplexing function (MPF) can control a multi-beam field emission x-ray (MBFEX) generating device XGD to generate specific multiplexing x-ray beams XB1, XB2, and XBk and direct the generated x-ray beams toward object O from different projection angles. In one example, the MPF controls the XGD to generate beams XB1, XB2, and XBk at a distinct temporal frequency $\omega_k$ by pixels (x, y) of x-ray generator XGD. After passing through object O, all x-ray beams XB1, XB2, and XBk can be detected by a high frame rate x-ray detector XD which outputs temporal data I(x, y, t) for every pixel. X-ray beams XB1, XB2, and XBk can have distinct waveforms. As described below, the distinct waveforms allow downstream processing components to distinguish the data obtained from the different projection angles.

The temporal data set can be processed by a demultiplexing function (DMPF) to extract projection images PI1, PI2, and PIk. These projection images can be combined to generate 3-D tomographic image data ID of the object. For example, the DMPF can include a temporal Fourier transform function (TFT) operable to obtain frequency domain spectrum I(x, y, $\omega$) based on the temporal data. Noise in the temporal data may be filtered by a numerical n-band filter for obtaining n distinct principle components d(x, y, $\omega_k$). An exemplary noise filter is described in U.S. patent application Ser. No. 11/410,997 to Lu et al., entitled "X-Ray Imaging Systems and Methods Using Temporal Digital Signal Processing for Reducing Noise and for Enhancing Imaging Acquisition Speed by Obtaining Multiple Images Simultaneously," the disclosure of which is incorporated herein by reference in its entirety.

The principle components generated by function TFT can correspond to a particular x-ray beam generated by x-ray generator device XGD. In particular, the principle components can correspond to x-ray beams XB1, XB2, and XBk. The kth principle component generated by function TFT corresponds to x-ray beam XBk generated from x-ray generator device XGD operating at $\omega_k$ frequency. Further, the principle components can be used to form projection image data PI1, PI2, and PIk from x-ray beams XB1, XB2, and XBk. The distinct waveform frequencies allow function TFT to distinguish the data obtained from the different projection angles. As a result, a number n of projection images can simultaneously be obtained during an exposure time of a single projection image using only one detector. Thus, a system according to the subject matter described herein can advantageously increase projection image data acquisition speed by n-fold over conventional CT systems.

Projection image data PI1, PI2, and PIk can be communicated to a image processing module IPM operable to combine the projection image data into three-dimensional tomographic image data ID of object O. Image data ID can be communicated to a display D operable to display a three-dimensional image of object O based on image data ID.

Figure 2:
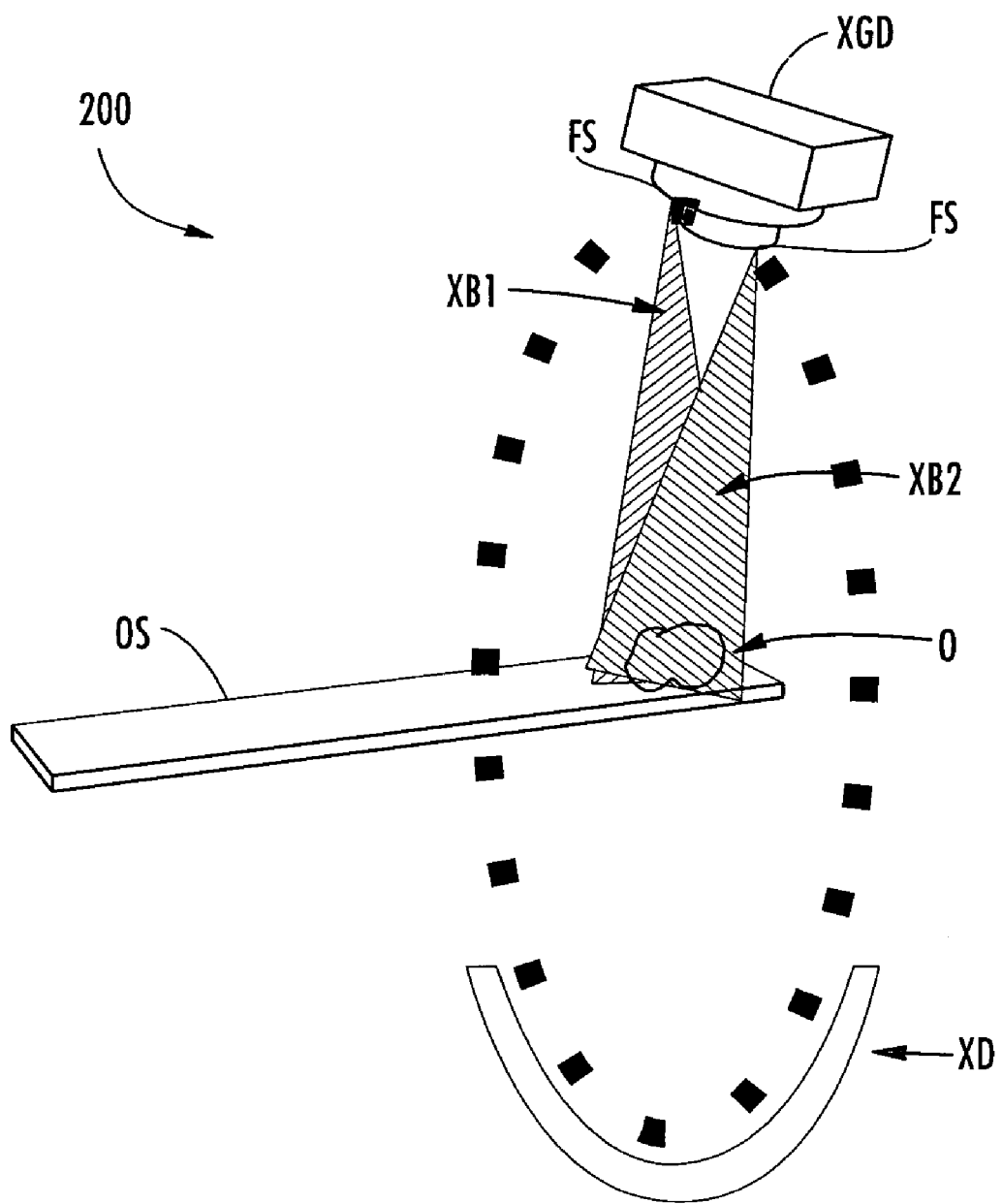
FIG. 2 illustrates a perspective side view of a multiplexing CT system according to the subject matter described herein.

FIG. 2 illustrates a perspective view of an exemplary multiplexing CT system generally designated 200 according to an aspect of the subject matter described herein. Referring to FIG. 2, multiplexing CT system 200 can comprise an x-ray generating device XGD comprising a multi-beam field emission x-ray source operable to generate a plurality of x-ray beams XB1 and XB2 from a plurality of focal spots on the x-ray anode surface.

X-ray generating device XGD can have an anode shaped with a ring-shaped geometry with focal spots FS arranged for forming 360 degree viewing angles. In particular, the generated x-ray beams are directed towards a center of the ring-shape for targeting object O positioned on an object stage OS. An x-ray detector XD can be positioned for receiving x-ray beams that pass through or past object O. Each focal spot FS can be equal distance to object O.

In one aspect, in order to provide sufficient projection images for CT reconstruction by an image processing module, the number of focal spots required can be in the range of about 100 to about 3,000 and covering over about 180 degrees to about 360 degrees of viewing angles.

In another aspect, for applications in limited angle tomographic imaging modalities such as laminography and tomosynthesis, the total number of projection images and the range of the viewing angles can be smaller. For breast tomosynthesis applications, it is envisioned that x-ray beams covering about 30-50 degrees viewing angles may be sufficient.

Figure 3:
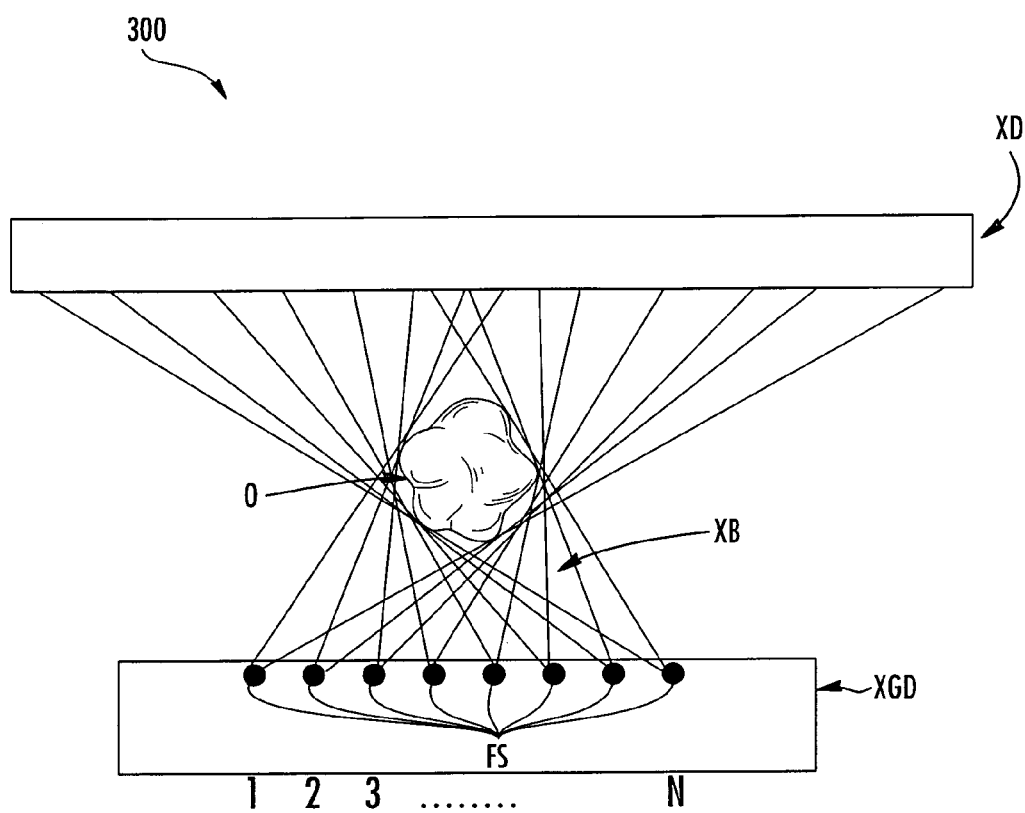
FIG. 3 illustrates a front view of a stationary, planar multiplexing CT system according to the subject matter described herein.

FIG. 3 illustrates a schematic diagram of a stationary, planar multiplexing CT system 300 according to an aspect of the subject matter described herein. Referring to FIG. 3, x-ray generator device XGD includes a plurality of focal spots (1–N), such as focal spots FS, positioned on an anode surface. Focal spots FS can be configured to emit x-ray beams, generally designated XB, when bombarded by x-rays from an x-ray source. X-ray beams XB can each having distinct waveforms. X-ray beams XB can be directed toward object O from a plurality of different viewing angles. X-ray detector XD can be configured for detecting the x-ray beams passing through or past object O. In particular, x-ray detector XD can detect the x-ray intensities of the x-ray beams passing through or past object O as a function of time. An image processing module can extract individual projection image data from the detected x-ray intensities based on the distinct waveforms of the x-ray beams for combining the projection image data to generate three-dimensional tomographic image data of the object. The three-dimensional tomographic image data can be stored and/or used by a suitable display for displaying a three-dimensional image of object O.

Figure 4:
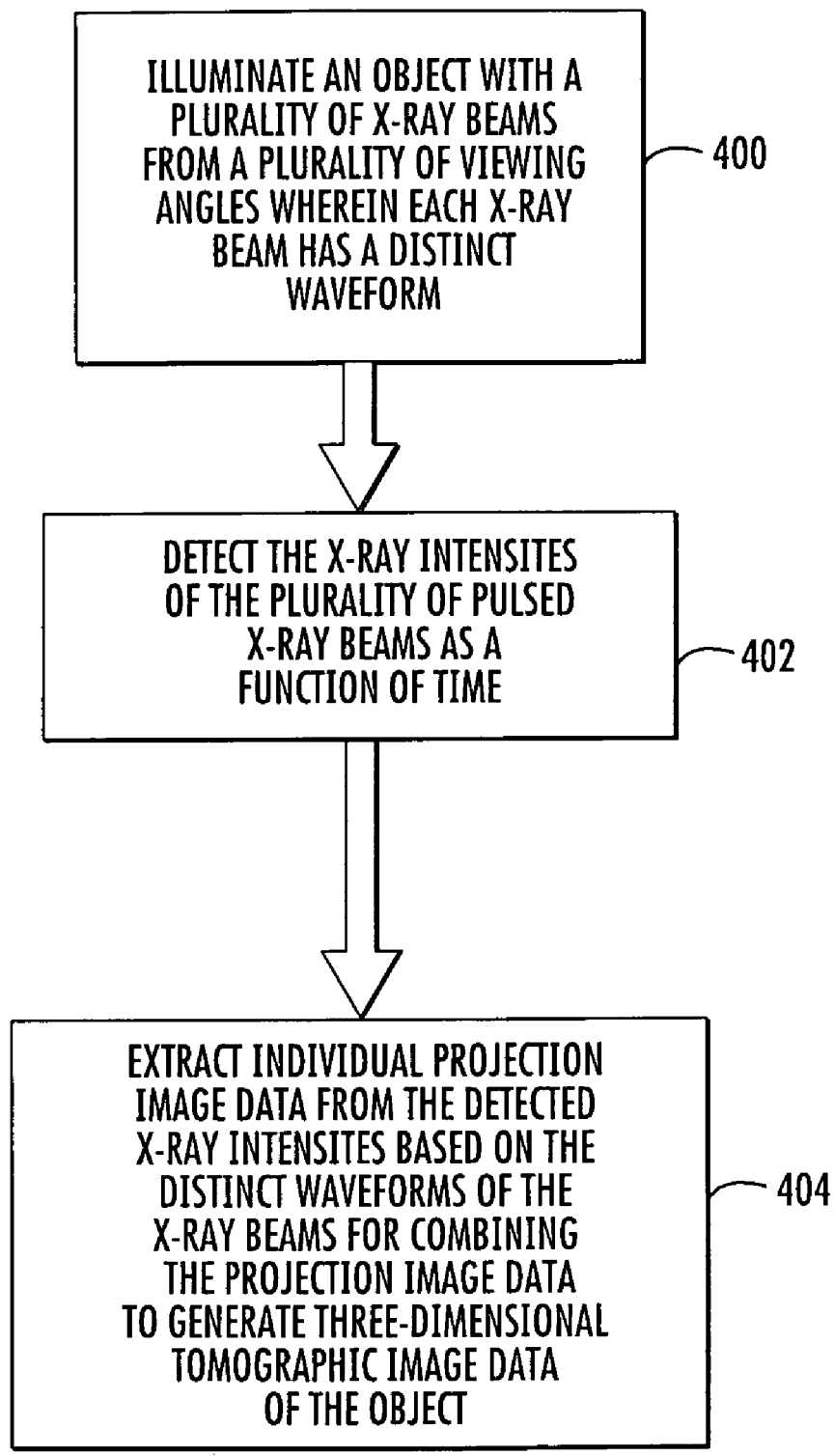
FIG. 4 is a flow chart of a process for performing multiplexing computed tomography according to the subject matter described herein.

FIG. 4 is a flow chart of an exemplary process for performing multiplexing computed tomography according to an aspect of the subject matter described herein. Referring to FIG. 4, in block 400, an object is illuminated by a plurality of x-ray beams from a plurality of viewing angles. Each x-ray beam can have a distinct waveform, which is controlled by multiplexing function MPF. For example, x-ray generator device XGD shown in FIG. 1 can be controlled to generate x-ray beams XB1, XB2, and XBk having distinct temporal waveforms and direct the x-ray beams toward object O. In block 402, the x-ray intensities of the plurality of x-ray beams can be detected as a function of time. For example, referring again to FIG. 1, the x-ray beams illuminating object O can be detected by x-ray detector XD. In one example, the x-ray detector can be an array or an area digital x-ray detector wherein the frame rate of the detector is faster than pulse rates of the x-ray beams.

In block 404, individual projection image data can be extracted from the detected x-ray intensities by a demultiplexing function DMPF corresponding to the specific MPF. The extracted individual image data can be combined to generate three-dimensional tomographic image data of the object.

Further, in block 404, a three-dimensional image of the object based on the generated three-dimensional image data of the object can be displayed. For example, referring again to FIG. 1, display D can display a three-dimensional image of object O based on the generated three-dimensional image data ID of object O.

By using systems and methods in accordance with the subject matter described herein, the total time required to collect all the projection images from all the viewing angles can be significantly reduced. For example, assume that 1,000 projection images are required for reconstruction and each image requires 500 μs. Conventional CT scanners using a serial approach can take 1,000 exposures sequentially, at 500 μs. The process can take 0.5 seconds. However, multiplexing a plurality of simultaneous x-ray beams in accordance with examples of the subject matter described herein, which can generate x-ray beams of distinct waveforms simultaneously, reduces the total exposure time of the entire scan to 1 millisecond, which is 500 times faster than the conventional serial method (0.5 s) without sacrificing the imaging quality.

Further, by using systems and methods in accordance with the subject matter described herein, requirements for the x-ray intensity can be significantly reduced and image data collection times can be reduced or at least equal to the total image data collection time required of conventional serial CT scanner. For comparison, the same example discussed above is used. Assuming 1000 projection images are required for reconstruction and each image requires 500 μs×1 Ampere x-ray dose, conventional CT scanners with a serial approach can capture 1000 exposures sequentially, at 500 μs×1 Ampere x-ray dose each. This process will require about 0.5 second. For comparison purposes, a system in accordance with the subject matter described herein including 1000 x-ray emitting pixels covering more than 180 degree viewing angle range is used. In this example, all of the x-ray beams of the x-ray generator device are turned on simultaneously. Each x-ray beam is pulsed at a different frequency. In a more specific aspect, each x-ray beam has a square waveform and a 50% duty cycle. The frequency range of the 1000 x-ray beams is between f and 3f, where f is the lowest frequency of the group. Instead of using 1 Ampere (A) tube current as in conventional systems, the value is reduced to 0.1 A tube current for each pixel. To keep the same x-ray dose per exposure, the total exposure time of each beam is increased by a factor of 10. Thus, for the multiplexing CT process, each x-ray beam is on for 10 milliseconds (500 μs×10/50%). The x-ray tube current of each pulse is 0.1 A. Since all of the beams are on at the same time, the total exposure time of the entire scan is 10 milliseconds, which is 50 times faster than in a conventional system using the serial method (0.5 second). Further, the x-ray tube current required is only 10% of that used for conventional CT scanners and without sacrificing imaging quality. The reduction in the x-ray tube current made possible by the subject matter described herein can be important, for example, because lower tube current results in lower costs, longer system lifetime, and smaller size as compared to conventional systems.

In one aspect, the subject matter described herein can be used in accordance with energy subtraction imaging techniques. In energy subtraction techniques, two or more images of the same object can be taken using x-ray beams having different energy levels. In one example, the x-ray beams having different energy levels are applied sequentially to an object, wherein a first image of the object is captured using an x-ray beam having energy level E1, and subsequently a second image of the object is captured using a second x-ray beam having energy level E2. In this example, an x-ray generator device can be controlled such that x-ray beams are generated with differing energy levels wherein energy level E1 is slightly above an absorption edge of the object and energy level E2 is slightly below the absorption edge of the object. Assuming the object does not move, the x-ray intensity of one image can be subtracted from the x-ray intensity of the second image to increase the contrast of the elements of interest. However, objects in motion can cause difficulty in registering the two images.

In one aspect using energy subtraction imaging techniques, two single-pixel x-ray sources and a digital x-ray detector can be used. Source 1 can be operated at an anode energy of E1, and source 2 can operated at an anode energy of E2. The two x-ray beams can be pulsed at frequencies of f1 and f2. The duty cycles of the two pulsed x-ray beams are higher than 50%. In this example, the two images of the object can be collected in a time shorter than required for capturing the images sequentially and with the same imaging quality. As a result, motion induced problems can be minimized.

Figure 5A:
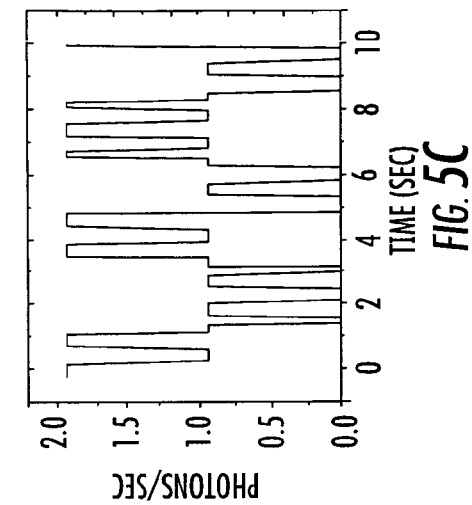
FIGS. 5A-5F are graphs of simulation results of a two-beam multiplexing CT system according to the subject matter described herein.
Figure 5B:
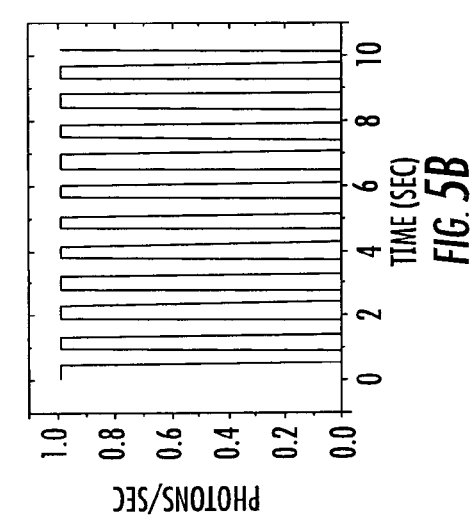
Figure 5C:
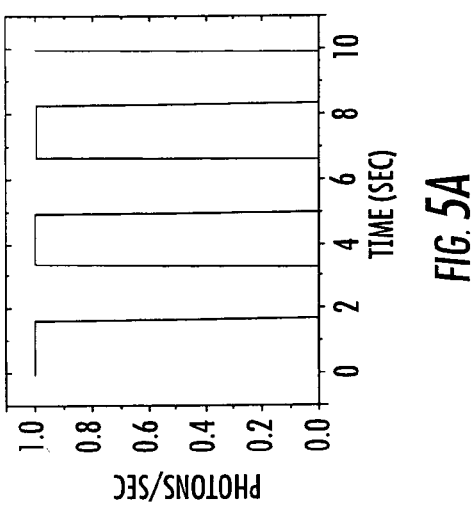
Figure 5D:
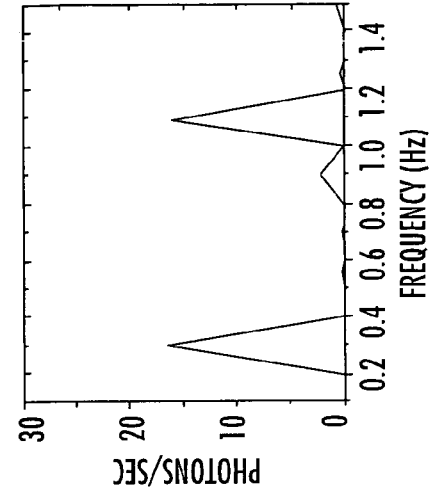
Figure 5E:
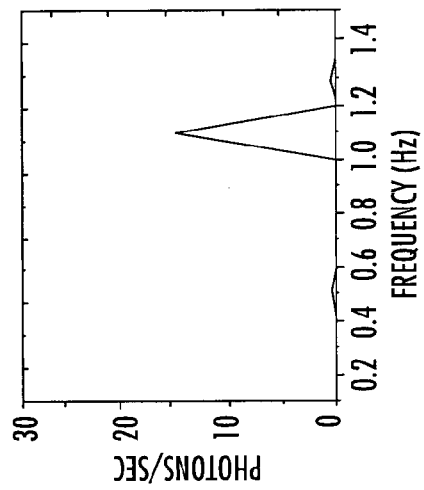
Figure 5F:
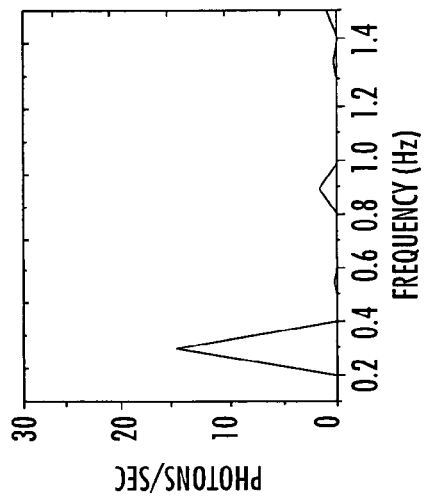
Figure 6A:
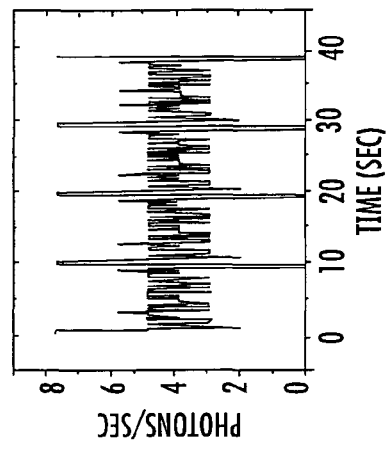
FIGS. 6A-6F are graphs of simulation results of an eight-beam multiplexing CT system according to the subject matter described herein.
Figure 6B:
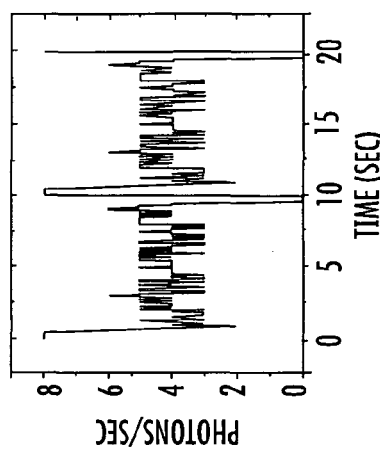
Figure 6C:
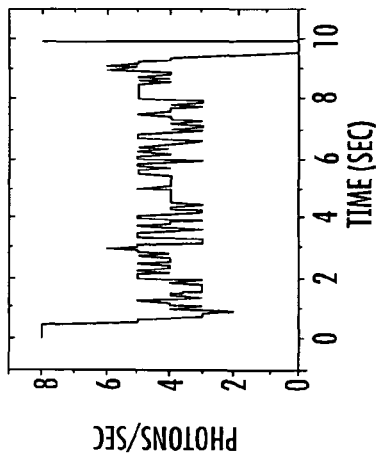
Figure 6D:
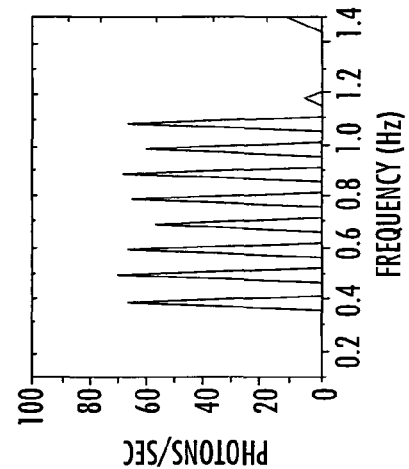
Figure 6E:
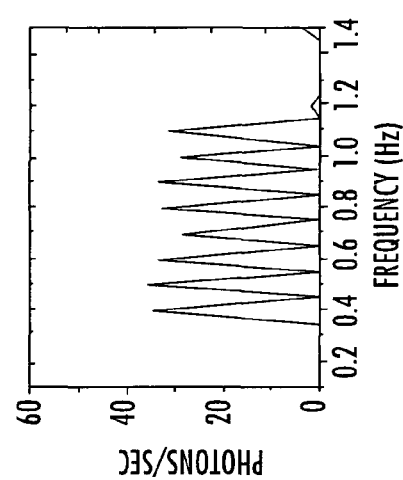
Figure 6F:
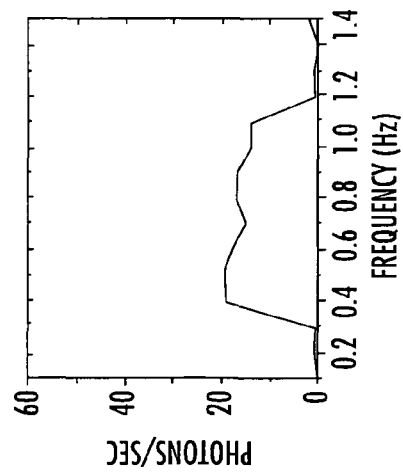

FIGS. 5A-5F and 6A-6F are graphs of simulation results of two- and eight-beam multiplexing CT systems, respectively, according to aspects of the subject matter described herein. The graphs of FIGS. 5A and 5B show x-ray intensity versus time data for first and second x-ray beams, respectively, generated by a system in accordance with the subject matter described herein. X-ray intensity is measured in photons received per second, also referred to as counts per second. FIG. 5C shows the sum of the waveforms of the first and second x-ray beams. FIGS. 5D-5F show corresponding x-ray data in the frequency domain for each of the waveforms shown in FIGS. 5A-5C, respectively. The x-ray beams from the first and second x-ray beams are identifiable based on their frequencies in FIGS. 5D-5F. This data can be utilized by an image processing module for extracting individual projection image data from detected x-ray intensities based on the distinct waveforms of the x-ray beams for combining projection image data to generate three-dimensional tomographic image data of an object.

In FIG. 6, graphs 6A-6C show the total x-ray intensity recorded at a pixel of the x-ray detector, measured in photons per second, versus data acquisition time, measured in second, in the time domain generated by a eight-beam system in accordance with the subject matter described here. FIGS. 6D-6F show corresponding x-ray data in the frequency domain. However, the x-ray beam waveform is not clearly identifiable in FIG. 6D because the acquisition time is too small. The x-ray beams, as illustrated in FIGS. 6E-6F, are clearly resolved in the frequency domain for acquisition times greater than 20 seconds. Therefore, projection image data for sufficiently high acquisition times can be utilized to generate three-dimensional tomographic image data of an object.

Figure 7:
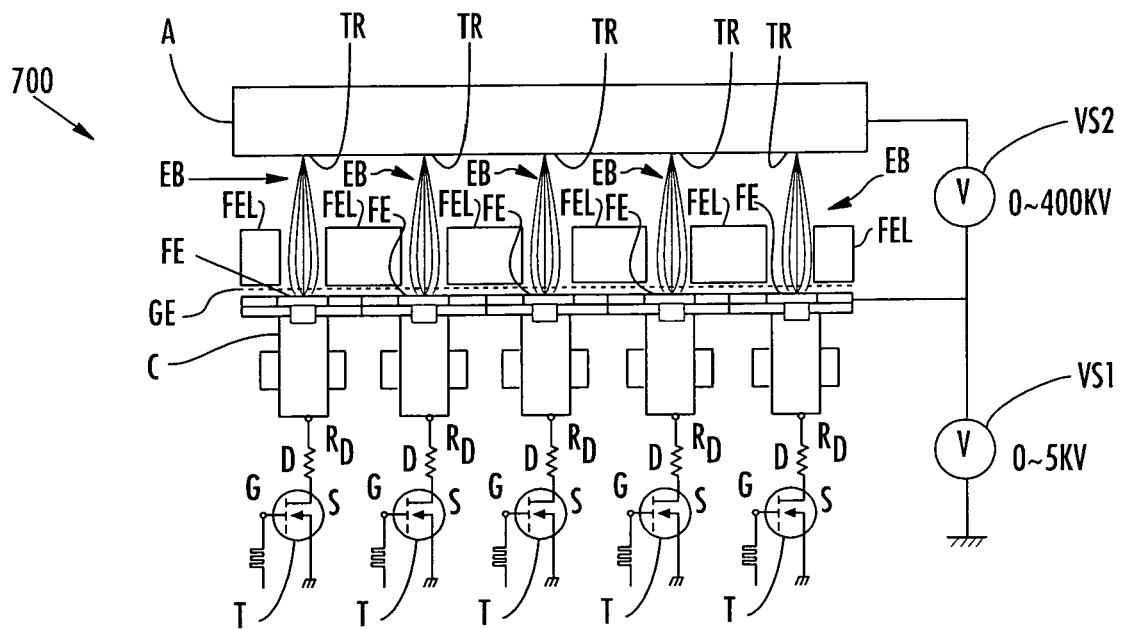
FIG. 7 is a schematic, cross-sectional side view of a multi-pixel, field emission x-ray source according to the subject matter described herein.

In one aspect, an x-ray generating device according to the subject matter described herein can comprise a multi-pixel field emission x-ray source operable to simultaneously generate x-ray beams having distinct waveforms. The multi-pixel field emission x-ray source can direct the x-ray beams toward an object in accordance with the subject matter described herein. FIG. 7 is a schematic, cross-sectional side view of a multi-pixel field emission x-ray source generally designated 700, according to an aspect of the subject matter described herein. Referring to FIG. 7, x-ray source 700 can include a plurality of electron field emitters FE for emitting electrons. Electron field emitters FE can comprise one or more carbon nanotubes and/or other suitable electron field emission materials. Further, electron field emitters FE can be attached to a surface of respective cathodes C, conductive or contact line, or other suitable conductive material. Electron field emitters can be carbon nanotubes.

In another aspect, an x-ray generating device according to the subject matter described herein can comprise a multi-pixel field emission x-ray source configured to simultaneously generate a plurality of x-ray beams having distinct x-ray energy characteristics. The multi-energy x-ray beams can be used to obtain 3-D tomographic images with material properties or attributes in addition to the x-ray attenuation coefficient, otherwise known as the CT number, for medical imaging applications. These attributes can include, for example, the chemical composition, atomic number, or density of an object. Exemplary applications can also include detecting the chemical composition of an object, for bomb detection and homeland security purposes. In an alternative example, cancer tissue may be distinguishable from normal tissue by its elastic properties, or may contain certain elements such as calcium, which may be determined using a multi-energy x-ray imaging system according to the subject matter described herein for use in medical applications.

Electron field emitters FE can be controlled by a suitable controller, such as suitable general-purpose computer, to emit electrons for producing respective electron beams EB. In one aspect, a controller can control voltage sources VS1 to apply voltages between electron field emitters FE and gate electrodes GE to generate respective electric fields for extracting electrons from electron field emitters FE. The applied voltages can be pulsed at different frequencies for generating pulsed electron beams EB of different frequencies. In particular, the controller can individually operate a plurality of metal-oxide-semiconductor field-effect transistors (MOSFETs) T for individually controlling field emitters FE to emit electrons. The controller can individually control the voltage applied to field emitters FE for individually turning transistors on and off. The drains of transistors T can be connected to a corresponding one of a plurality of cathodes C. Transistors T can be turned on and off by the individual application of a high signal (e.g., 5 V) and a low signal (e.g., 0 V), respectively, to the gates of transistors T. When a high signal is applied to the gate of a transistor, a drain-to-source channel of the transistor is turned on to apply a voltage difference between a respective cathode C and gate electrode GE. A voltage difference exceeding a threshold can generate an electric field between cathode C and gate electrode GE such that electrons are extracted from respective electron field emitters FE. Conversely, when a low voltage (e.g., 0 V) is applied to the gate of a transistor, a corresponding drain-to-source channel is turned off such that the voltage at electron field emitter FE is electrically floating and the voltage difference between a respective cathode C and gate electrode GE cannot generate an electric field of sufficient strength to extract electrons from the respective electron field emitter. The controller is operable to individually apply voltage pulses of different frequencies to the gates of transistors T. Thus, the controller can individually control the frequencies of the electron beam pulses from field emitters FE.

Further, x-ray source 700 can include an anode A having a plurality of focus spots bombarded by a corresponding electron beam. A voltage difference can be applied between anode A and gate electrode GE such that respective fields are generated for accelerating electrons emitted by respective electron field emitters FE towards respective target structures TR. Target structures TR can, for example, be made of molybdenum. Target structures TR can produce x-ray beams having a desired pulse frequency upon bombardment by electron beams EB. X-ray source 800 can include a focusing electrode FEL for focusing electrons extracted from electron field emitters FE on target structure T and thus reduce the size of electron beam EB. Focusing electrode FEL can be controlled by application of voltage to focusing electrode FEL by voltage source VS2. The gate voltage can be varied depending on required flux.

Electron field emitters FE and gate electrode GE can be contained within a vacuum chamber with a sealed interior. The interior of vacuum chamber can be evacuated to achieve a desired interior pressure. Electron beam EB can travel from the interior of vacuum chamber to its exterior through an electron permeable portion or window. In one example, the electron permeable portion or window can be 4" diameter beryllium (Be) x-ray window. X-ray beams of distinct waveforms can be generated by the electron bombardment of anode A by electron beams of distinct waveforms. Further, anode A can be suitably shaped and/or angled such that the generated x-ray beams are transmitted toward an object from a plurality of different viewing angles.

Figure 8:
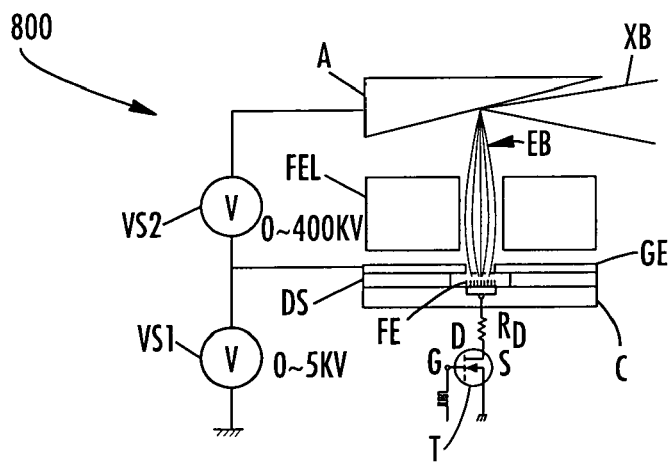
FIG. 8 is a schematic, cross-sectional side view of an x-ray unit of the x-ray source shown in FIG. 8 for generating a single, pulsed x-ray beam according to the subject matter described herein.

FIG. 8 is a schematic, cross-sectional side view of an x-ray unit generally designated 800 of x-ray source 700 shown in FIG. 7 for generating a single, pulsed x-ray beam XB according to an aspect of the subject matter described herein. X-ray unit 800 represents a single pixel of x-ray source 700. Referring to FIG. 8, x-ray unit 800 can include an electron field emitter FE deposited on a cathode C. In one example, electron field emitter FE can be a 1.5 mm diameter carbon nanotube film. The carbon nanotube film can be deposited on a surface of a metal substrate. Further, the carbon nanotube film can be deposited on the surface by an electrophoretic process.

X-ray unit 800 can include a gate electrode GE for extracting electrodes on application of voltage by voltage source VS1. In one example, gate electrode GE can be a tungsten grid. Gate electrode GE can be spaced from cathode C by a dielectric spacer DS.

In one aspect, x-ray beam XB can be generated by applying a constant DC voltage to anode A and a variable DC voltage to gate electrode GE. An n-channel MOSFET T can be adapted for switching on and off the emission of electrons from electron field emitter FE. A pixel can be activated by applying a 5V signal to open the channel of MOSFET T such that electron field emitter FE forms a complete electrical circuit with gate electrode GE. Electron field emitter FE can be electrically coupled to a drain of MOSFET T. The source of MOSFET T can be grounded. The gate of MOSFET T can be connected to the output of a digital I/O board adapted to provided a 5 V DC voltage signal.

Electrons can be emitted from field emitter FE when the voltage applied by voltage source VS1 is greater than the critical field for emission. The emitted electrons can be accelerated by application of a voltage across anode A and gate electrode GE by voltage source VS2. The electrons form an electron beam EB that bombard an area of anode A to generate x-ray beam XB. A voltage can be applied to a focusing electrode FEL for focusing electron beam EB onto a target focal spot of anode A.

Referring again to FIG. 7, a scanning x-ray beam from different origins on a target of anode A can be produced by sweeping a pulsed controlling signal having a predetermined pulse width across each MOSFET in x-ray source 700. At each MOSFET that the signal is swept, a channel of the MOSFET can be opened for producing an x-ray beam from the corresponding focal point on the anode target.

A subset of the pixels can be activated such that the subset of pixels emits electrons with the same pulsing frequencies which generate x-ray beams from different focal points with the same frequencies. Alternatively, a pixel subset can be activated such that the subset of pixels emits electrons with different pulsing frequencies which generate x-ray beams from different focal points with different frequencies. In one aspect, a subset of pixels can be activated by using separate gate electrons for the subset of pixels. Extraction voltages can be applied to the corresponding pixels with predetermined pulsing frequencies to generate field emitted electrons with the desired pulsing frequencies and amplitudes.

In another aspect, a subset of pixels can be activated by using a common gate for all of the electron emitting pixels. The electron beam can be pulsed by pulsing the activation voltage applied to the MOSFET circuit. For example, in order to generate a pulsed x-ray beam with a predetermined frequency, a pulsed voltage with the predetermined frequency can be applied to open the corresponding MOSFET.

Figure 9A:
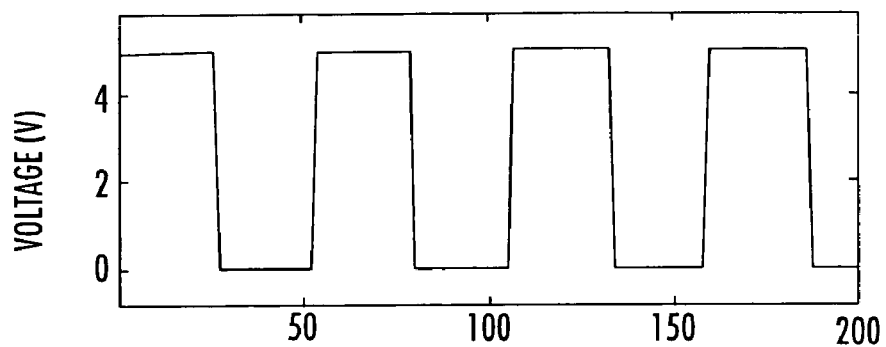
FIGS. 9A-9C are graphs illustrating the sum of two x-ray waveforms experimentally measured by an x-ray intensity detector.
Figure 9B:
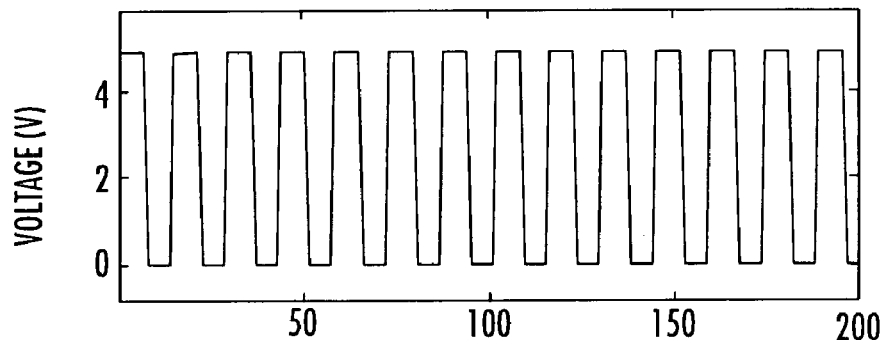
Figure 9C:
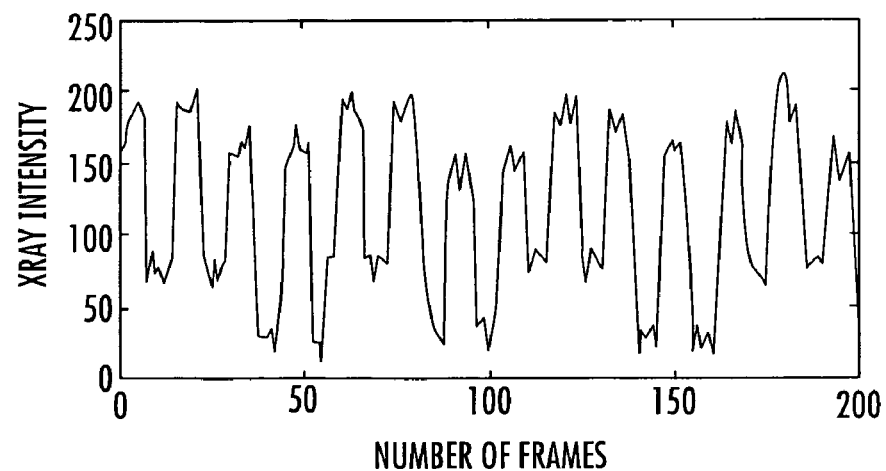

FIGS. 9A-9C are graphs of the sum of experimental results of a two-beam multiplexing CT system according to an aspect of the subject matter described herein. FIGS. 9A and 9B show exemplary waveforms displayed as a function of voltage versus the number of frames. FIG. 9C shows the experimentally measured x-ray intensity, measured in photons per second resulting from sum of these two waveforms. This data may be utilized by an image processing module for extracting individual projection image data from detected x-ray intensities based on the distinct waveforms of the x-ray beams for combining projection image data to generate three-dimensional tomographic image data of an object.

Figure 10:
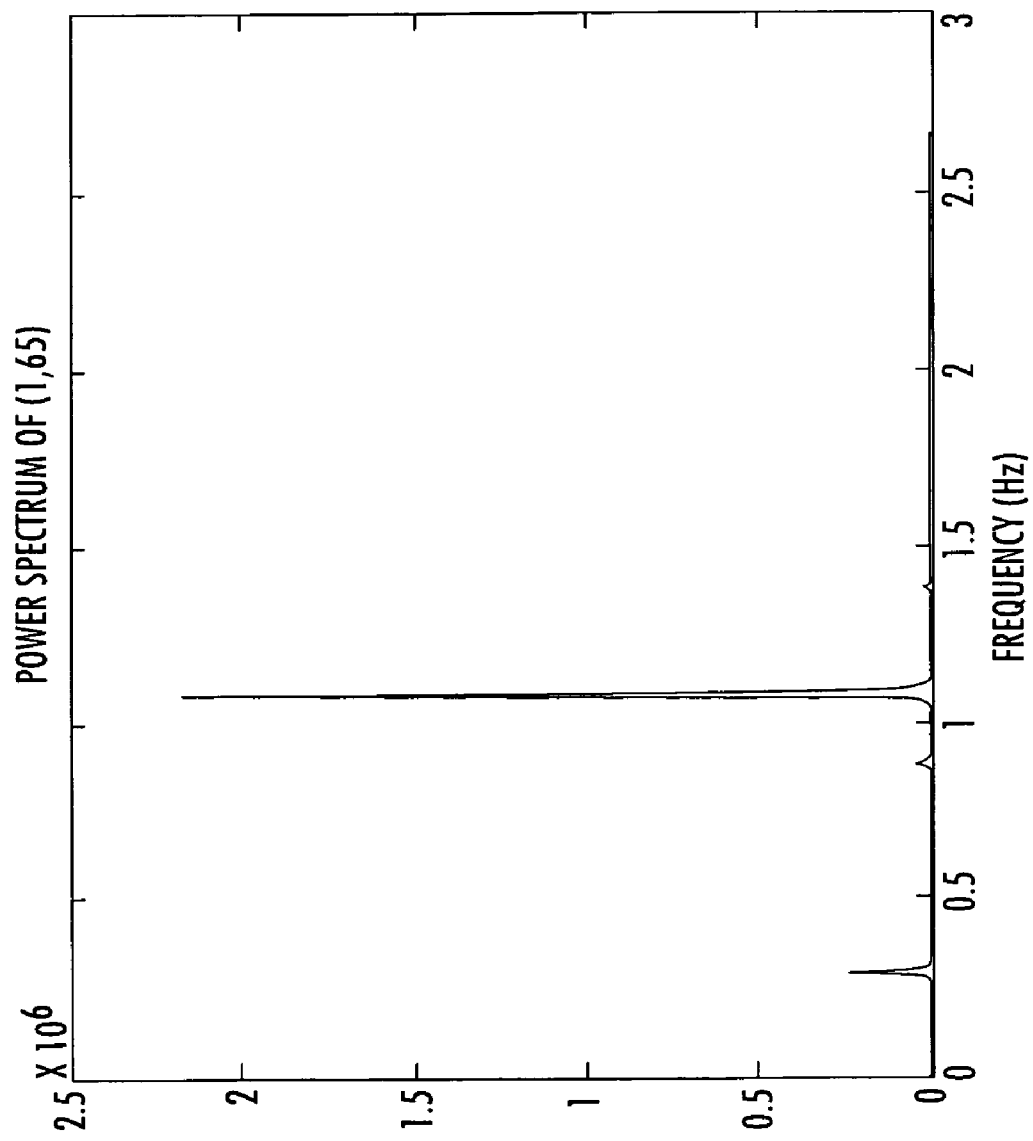
FIG. 10 is a graph of two x-ray beams with square waveforms after a Fourier transform has been performed on the data.

FIG. 10 shows two x-ray beams with square waveforms after a temporal Fourier transform has been performed on the data, which can be a component of image processing module IPM.

Figure 11:
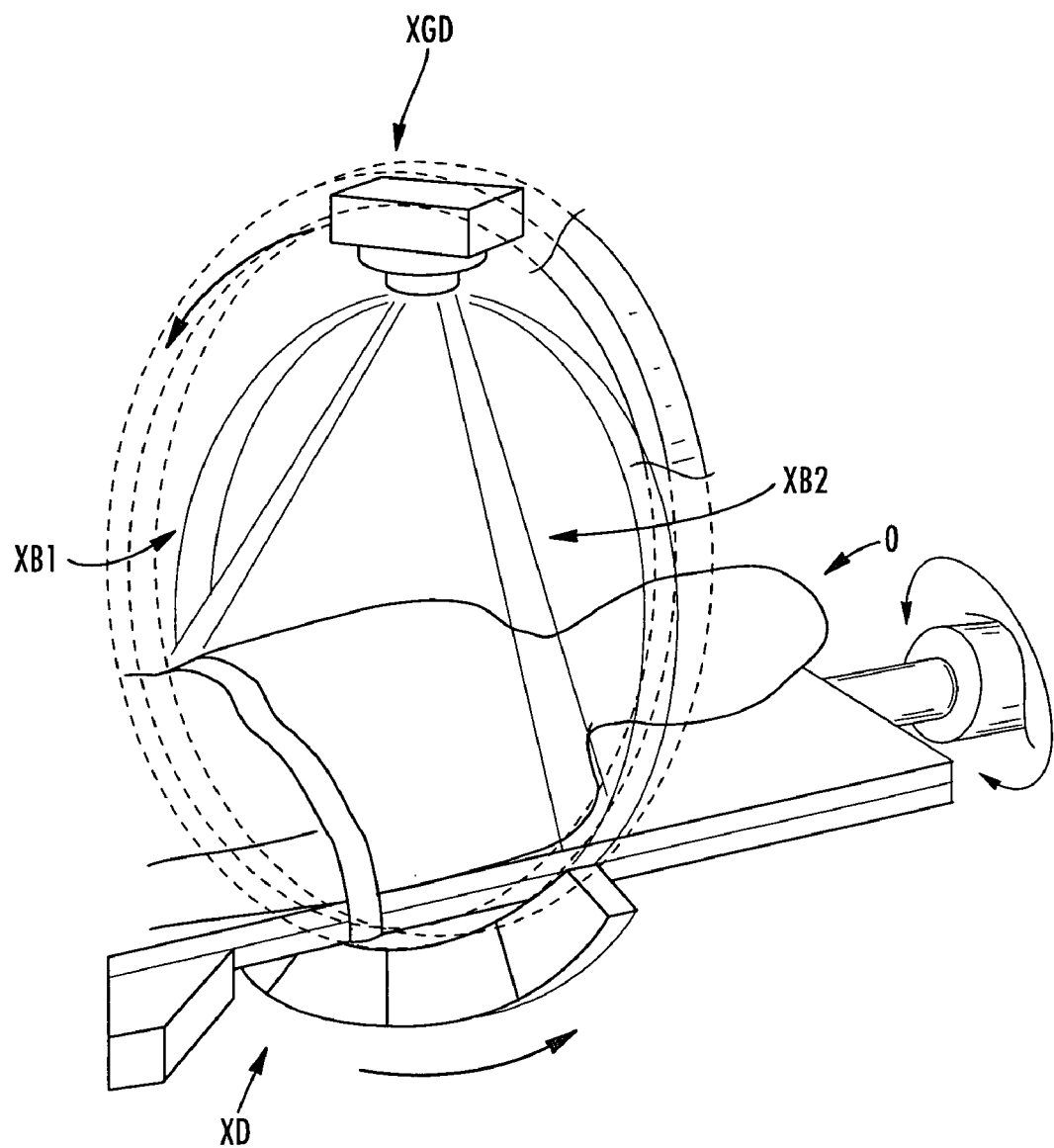
FIG. 11 illustrates a perspective side view of a multiplexing CT system with a rotating gantry and movable object stage according to the subject matter described herein.

FIG. 11 shows an x-ray source and x-ray detector which can rotate around an object to be imaged using a gantry. Moreover, the object stage can be configured to rotate, so that images can be acquired from multiple angles.

The following U.S. patents and applications are related to the subject matter described herein, and are incorporated herein by reference in their entireties. X-ray generating devices described in U.S. Pat. Nos. 6,553,096 and 6,850,595 (both entitled "X-Ray Generating Mechanism Using Electron Field Emission Cathode"), the disclosures of which are incorporated herein by reference in their entireties, disclose x-ray generating devices including a field emission cathode formed at least partially from a nanostructure-containing material. The x-ray generating devices disclosed in these patents are examples of x-ray generating devices for use in accordance with the subject matter described herein.

Yet another exemplary x-ray generating device is described in U.S. Pat. No. 7,082,182 (entitled "Computed Tomography System for Imaging of Human and Small Animal"), the disclosure of which is incorporated herein by reference in its entirety. This patent discloses a computed tomography device comprising an x-ray source and an x-ray detecting unit. The x-ray sources and x-ray detecting units disclosed in this patent application are examples of x-ray generating devices and x-ray detectors for use in accordance with the subject matter described herein.

An exemplary method and system for CT imaging of oscillatory objects is described in pending U.S. patent application Ser. No. 11/051,332 to Zhou et al. (entitled "Computed Tomography Scanning System and Method Using a Field Emission X-Ray Source"), the disclosure of which is incorporated herein by reference in its entirety. This application discloses an exemplary micro-computed tomography scanner comprising a micro-focus field emission x-ray source, an x-ray detector, an object stage placed between the x-ray source and the detector, an electronic control system and a computer that controls the x-ray radiation and detector data collection, and computer software that reconstructs the three dimensional image of the object using a series of projection images collected from different projection angles. The x-ray beams being pulsed in a relationship with the motion of the object to be imaged. The x-ray sources and x-ray detecting units disclosed in this patent application are examples of x-ray generating devices and x-ray detectors for use in accordance with the subject matter described herein.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method of multiplexing computed tomography for simultaneous recording of a plurality of projection images of an object, the method comprising:
   (a) illuminating an object with a plurality of x-ray beams from a plurality of viewing angles, wherein each x-ray beam has a distinct waveform;
   (b) detecting the x-ray intensities of the plurality of x-ray beams as a function of time; and
   (c) extracting individual projection image data from the detected x-ray intensities based on the distinct waveforms of the x-ray beams for combining the projection image data to generate three-dimensional image data of the object, wherein extracting individual projection image data from the detected x-ray intensities comprises:
      (i) performing temporal Fourier transformation of the intensity versus time data;
      (ii) determining the intensity contribution from each of the x-ray beams based on a spectrum in a frequency space; and
      (iii) constructing the projection image data from each of the x-ray beams based on the extracted x-ray intensity from the frequency space.

2. The method of claim 1 wherein illuminating the object with a plurality of x-ray beams comprises illuminating the object with a plurality of x-ray beams individually controllable to emit x-ray beams simultaneously and in any time sequence, and are controllable to vary the frequency, duty cycle, and intensity of the waveforms of the x-ray beams.

3. The method of claim 1 wherein illuminating the object with a plurality of x-ray beams comprises illuminating the object with a plurality of x-ray beams emitted from a plurality of focal spots arranged such that x-ray images of the object are formed from 360 degree viewing angles.

4. The method of claim 1 wherein illuminating the object with a plurality of x-ray beams comprises illuminating the object with a plurality of x-ray beams generated by an x-ray generating device including a plurality of electron emitting pixels comprising carbon nanotubes or nanowires.

5. The method of claim 1 wherein extracting individual projection image data from the detected x-ray intensities for combining the data to generate three-dimensional tomographic image data of the object is performed by an application specific integrated circuit (ASIC) and an image reconstruction algorithm.

6. The method of claim 1 wherein extracting individual projection image data from the detected x-ray intensities for combining the data to generate three-dimensional tomographic image data of the object comprises displaying a three-dimensional image of the object based on the generated three-dimensional image data of the object.

7. The method of claim 1, wherein the x-ray intensities are detected at a frame rate equal to at least twice the frequency of the x-ray beam with the highest frequency.

8. The method of claim 1, wherein the distinct waveform of each x-ray beam comprises a distinct temporal waveform comprising a periodic function with a distinct frequency.

9. A computer program product comprising computer executable instructions embodied in a non-transitory computer readable medium for performing steps comprising:
   (a) illuminating an object with a plurality of x-ray beams from a plurality of viewing angles, wherein each x-ray beam has a distinct waveform;
   (b) detecting the x-ray intensities of the plurality of x-ray beams as a function of time; and
   (c) extracting individual projection image data from the detected x-ray intensities based on the distinct waveforms of the x-ray beams for combining the projection image data to generate three-dimensional image data of the object, wherein the projection image data comprises intensity versus time data for each of the x-ray beams, and wherein extracting individual projection image data from the detected x-ray intensities comprises:
      (i) performing temporal Fourier transformation of the intensity versus time data;
      (ii) determining the intensity contribution from each of the x-ray beams based on a spectrum in a frequency space; and
      (iii) constructing the projection image data from each of the x-ray beams based on the extracted x-ray intensity from the frequency space.

10. The computer program product of claim 9 wherein illuminating the object with a plurality of x-ray beams comprises illuminating the object with a plurality of x-ray beams individually controllable to emit x-ray beams simultaneously and in any time sequence, and are controllable to vary the frequency, duty cycle, and intensity of the waveforms of the x-ray beams.

11. The computer program product of claim 9 wherein illuminating the object with a plurality of x-ray beams comprises illuminating the object with a plurality of x-ray beams emitted from a plurality of focal spots arranged such that x-ray images of the object are formed from 360 degree viewing angles.

12. The computer program product of claim 9 wherein extracting individual projection image data from the detected x-ray intensities for combining the data to generate three-dimensional tomographic image data of the object is performed by an application specific integrated circuit (ASIC).

13. The computer program product of claim 9, wherein the distinct waveform of each x-ray beam comprises a distinct temporal waveform comprising a periodic function with a distinct frequency.

* * * * *

UNITED STATES PATENT AND TRADEMARK OFFICE
CERTIFICATE OF CORRECTION

PATENT NO. : 8,155,262 B2  
APPLICATION NO. : 11/526217  
DATED : April 10, 2012  
INVENTOR(S) : Zhou et al.

Page 1 of 1

It is certified that error appears in the above-identified patent and that said Letters Patent is hereby corrected as shown below:

At Column 1, Line 18 please replace the heading "GRANT STATEMENT" with

--GOVERNMENT INTEREST--

And

At Column 1, Line 20:

Please replace:

"This work was supported at least in part by grants from the National Institute of Health and the National Institute of Biomedical Imaging and Bioengineering (NIH-NIBIB) (Grant No. 1-R21-EB004204-01), and the National Institute of Cancer (NCI) (Grant No. U54CA119343). The U.S. government may have certain rights in the present disclosure."

With the following paragraph:

--This invention was made with government support under Grant Nos. 1-R21-EB004204-01 and U54CA119343 awarded by the National Institute of Health and the National Institute of Biomedical Imaging and Bioengineering, and the National Cancer Institute. The government has certain rights in the invention.--

Signed and Sealed this  
Third Day of July, 2012

David J. Kappos  
*Director of the United States Patent and Trademark Office*